United States Patent [19]

Sneider

[11] 4,223,810
[45] Sep. 23, 1980

[54] SYRINGE CLOSURE WITH ATTACHABLE NOZZLE

[76] Inventor: Vincent R. Sneider, 3422 Hallcrest Dr., Atlanta, Ga. 30319

[21] Appl. No.: 967,461

[22] Filed: Dec. 7, 1978

[51] Int. Cl.² ............................................. A61M 1/00
[52] U.S. Cl. .................................. 222/107; 222/568; 150/8; 128/247; 128/232
[58] Field of Search ................. 222/92, 107, 566, 567, 222/568, 569, 570; 150/8; 128/231, 232, 248, 251, 258, DIG. 24, 247; 292/256.6

[56] References Cited

U.S. PATENT DOCUMENTS

| | | | |
|---|---|---|---|
| 2,353,153 | 7/1944 | Ferrel | 128/232 |
| 2,664,893 | 1/1954 | Kempel | 128/232 |
| 3,424,218 | 1/1969 | Vanderbur, Jr. et al. | 150/8 |
| 3,667,461 | 6/1972 | Zamarra | 128/232 |
| 3,688,766 | 9/1972 | Kempel | 128/232 |

Primary Examiner—David A. Scherbel
Attorney, Agent, or Firm—Robert L. Niblack; Neil E. Hamilton

[57] ABSTRACT

A closure for a syringe of the feminine or enema type wherein the nozzle of the syringe is intended to be transported separately from the flexible bag. The neck of the flexible bag which has a bead is secured on a support ledge of an inner connecting member which threadably receives the nozzle. An outer connecting member having spaced internal flange members is snap fitted over the inner connecting member to engage a portion of the bag and resiliently hold it against the inner connecting member. In a preferred manner, an accommodating compartment is formed between the two connecting members to accommodate the bead of the bag.

8 Claims, 6 Drawing Figures

U.S. Patent  Sep. 23, 1980  Sheet 1 of 2  4,223,810
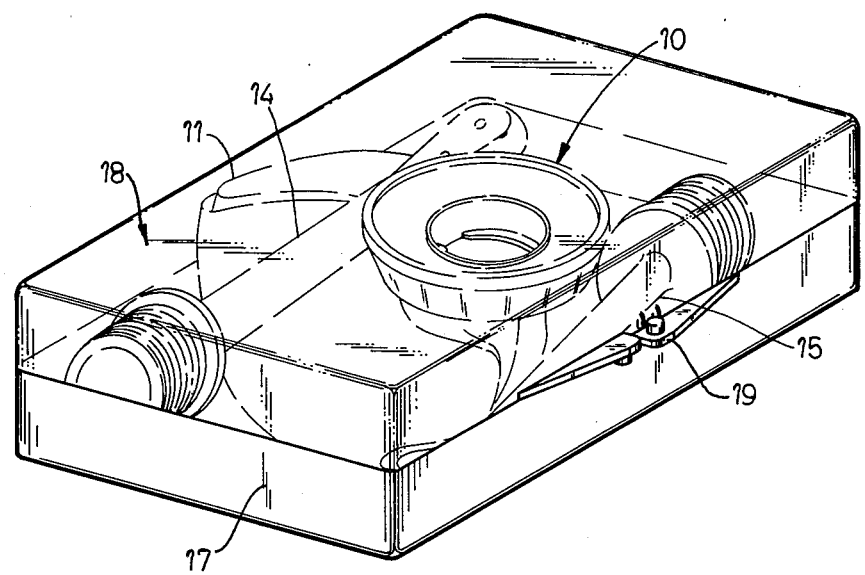
FIG.1
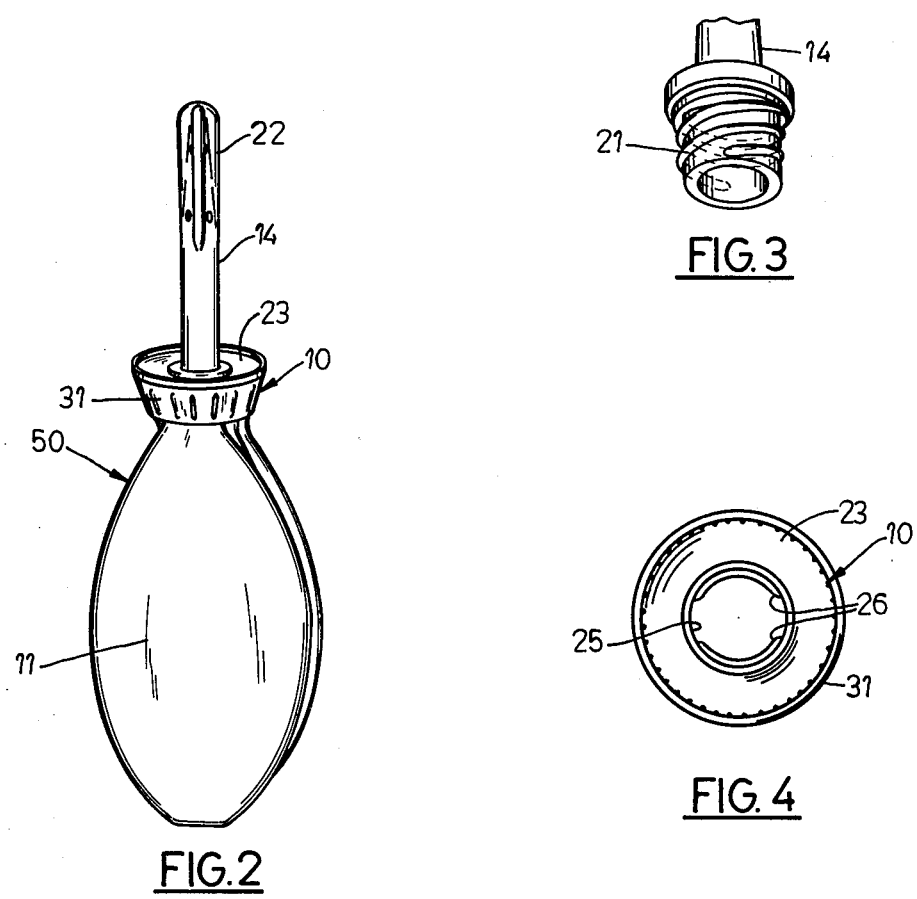
FIG.2
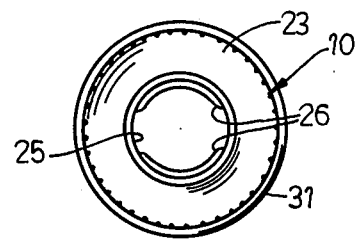
FIG.3
FIG.4

SYRINGE CLOSURE WITH ATTACHABLE NOZZLE

BACKGROUND OF THE INVENTION

This invention relates to a closure means for a syringe bag. More particularly, this invention relates to a connecting member which will provide a secure and fluid tight engagement with a syringe bag as well as with a syringe nozzle.

Closure means for the types of syringe bags concerned with in this invention are described in U.S. Pat. Nos. 3,144,866; 3,530,858; 3,589,362; 3,726,276; 3,773,047; 3,892,311 and 3,948,260. U.S. Pat. No. 3,773,047 and 3,892,311 disclose a disposable syringe unit wherein a snap fit arrangement is provided between a collar member secured to a nozzle and a tubular member with the bag secured therebetween. U.S. Pat. No. 3,726,276 shows a snap fit arrangement between a nozzle member and a bag whereas U.S. Pat. No. 3,589,362 shows a threaded fitment for a similar purpose. U.S. Pat. No. 3,144,866 is directed to a ratchet-type arrangement for securing a nozzle on a flexible bag with the bag secured in a threaded plug. In U.S. Pat. No. 3,530,858 a rubber band is employed as a means of securing a bag to a collar. U.S. Pat. No. 3,948,260 discloses an inner fitment member for a nozzle wherein the bag is seated on a ledge portion and by means of the elasticity of the bag is resiliently held on the ledge.

In some instances where the resiliency of the bag alone is relied upon for being retained on a connecting member for a syringe, problems can arise when greater than normal force is applied to the bag for purposes of expelling its contents. In such instances, the force has been known to cause the connecting member to become separated from the bag with the resultant undesired spraying and spilling of the contents of the bag in an uncontrolled manner.

It is an advantage of the present invention to provide a novel closure means for a syringe bag. Other advantages include a connecting means for a flexible bag wherein the bag is retained in a fluid tight manner on a connector for a removable nozzle; a connector which when assembled will maintain a resilient force to hold a portion of the bag against a connecting member; a connecting member which can be assembled onto a flexible bag in a fast and efficient manner and which can withstand substantial forces in excess of those normally employed in operating a syringe unit.

SUMMARY OF THE INVENTION

The foregoing advantages are accomplished and the shortcomings of the prior art are overcome by the present closure means which includes a first connecting member defining a hollow body section with internal connecting means for receiving a hollow nozzle member having a spray stem and external connecting means to be received by the internal connecting means of the first connecting member. A support ledge member extends from the body section of the first connecting member as well as a wall portion which is spaced from the support ledge member. A second hollow connecting member includes two spaced flange members extending internally in the direction of the second connecting member. The second connecting member is constructed and arranged in relation to the first connecting member so that the two connecting members are snap fitted together with the first connecting member being contained within the confines of the second connecting member and retained by the spaced flange members. In a preferred embodiment, the first connecting member is of a rigid construction and the second connecting member is semirigid so as to effect a resilient retention of the resilient bag wall against the ledge member of the inner connecting member.

BRIEF DESCRIPTION OF THE DRAWINGS

A better understanding of the present closure means will be accomplished by reference to the drawings wherein:

FIG. 1 is a perspective view illustrating the closure means of this invention in conjunction with a syringe bag and two syringe nozzles contained in a tray-like container and resulting in a traveling kit.

FIG. 2 is a perspective view of an assembled syringe unit utilizing the novel closure means.

FIG. 3 is a partial view in perspective showing the threaded end of a nozzle for engagement with the closure means.

FIG. 4 is a top plan view of the closure means in an assembled state and showing the threaded connection for the nozzle in FIG. 3.

DESCRIPTION OF THE PREFERRED EMBODIMENT

Figure 5:
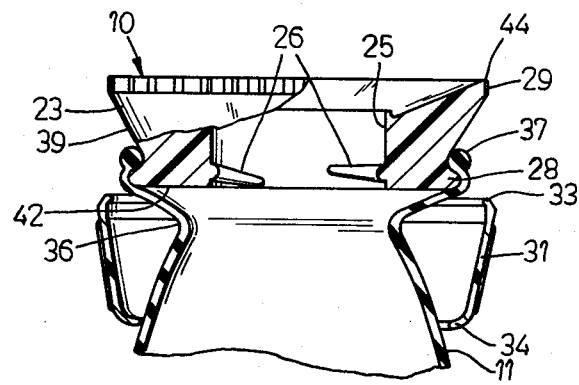
FIG. 5 is a view in side elevation and in partial vertical section showing the connector surrounding a flexible bag but in a pre-assembled state.

Proceeding to a detailed description of a preferred embodiment of the present invention, the closure means generally 10 is shown in connection with a flexible and collapsible bag 11. As best seen in FIG. 1, the closure 10 and bag 11 as well as the feminine spray nozzle 14 and a rectal spray nozzle 15 are packaged in a container 17 to result in a convenient traveling kit 18. The container 17 has the usual friction-fit-type, snap-open closure 19.

Referring specifically to FIGS. 2, 3 and 4, it will be seen that the closure means 10 has internal threads 26 to complementarily receive the external threads 21 on the feminine spray nozzle 14. Thread 21 and 26 are of the double helix type for quick insertion and removal of nozzle 14 from closure means 10. The assembled unit with the bag 11, closure means 10 and the hollow nozzle 14 with a spray stem outlet end 22 is shown in FIG. 2.

Figure 6:
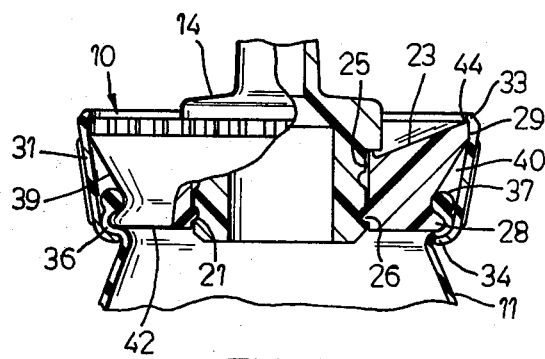
FIG. 6 is a view similar to FIG. 5 showing the connector in an assembled state on the flexible bag and with the nozzle member secured therein.

As best seen in FIGS. 5 and 6, the closure means 10 includes a first, annular, inner connecting member 23 having a hollow central portion 25 in which are disposed threads 26. A support ledge 28 extends annularly around the connecting member for accommodating a portion of bag neck 36 and annular bead 37. It will be noted that ledge 28 is coextensive with the base wall 42 of member 23. Inner connecting member 23 also has a reduced diameter portion 39 which terminates in an upper, laterally extending wall portion 29 which is coextensive with the top of the connecting member. A second hollow, annular, connecting member 31 is constructed to completely surround the inner connecting member 23 and has an annular flange member 33 at the top and a lower flange member 34 at the bottom. In a preferred manner, the inner connecting member 23 is formed of a rigid plastic material such as high density polyethylene. The outer connecting member 31 is formed from a flexible material such as low density polyethylene. In this manner, the flange member 34 will engage a portion of the base wall 42 adjacent support ledge 28 while allowing flange member 33 to frictionally snap over wall portion 29 to provide a snap fit arrangement with bead 37 resting against ledge 28 and housed in a compartment 40 formed between the outer connecting member 31 and the reduced diameter portion 39 of inner connecting member 23.

OPERATION

A better understanding of the advantages of closure means 10 will be had by a description of its operation. To assemble the closure means to bag 11, all that is required is placing the annular bead 37 of bag 11 against support ledge 28 as best shown in FIGS. 5 and 6. Previously, the outer connecting member 31 will be positioned over the bag neck and adjacent the base wall 42 of member 23, as best seen in FIG. 5. With bead 37 resting against support ledge 28, the outer connecting member 31 will be moved toward the inner connecting member 23 to completely surround it and cause flange 34 to impinge against bag 11 adjacent base wall 42 and at the same time permit flange 33 to engage over wall portion 29. Outer connecting member 31 is dimensioned so as to provide a snap fit relationship when flange member 34 engages the base of the ledge 28 and flange member 33 frictionally engages wall portion 29 and its upper surface as indicated by numeral 44. With the closure means 10 firmly secured to bag 11, the bag and closure will be folded and placed in container 17 along with the feminine spray nozzle 14 and the rectal spray nozzle 15. The resulting kit 18 is of a dimension such that it can be easily placed in a woman's purse or handbag and can conveniently be carried for traveling purposes.

When it is desired to utilize the contents of kit 18 all that is required is to fill the bag with water or a similar desired liquid and to select either of nozzles 14 or 15 by screwing them into closure means 10. The resulting syringe is indicated by the numeral 50 in FIG. 2.

An important aspect of the present invention is the unique snap fit arrangement between the outer connecting member 31 and the inner connecting member 23. The neck portion 36 will be held against support ledge 28 and retained therein under a biasing force due to the previously described snap fit arrangement. Due to the resilient nature of the bag material, it also will form in effect a gasket between the inner connecting member 23 and the outer connecting member 31 and at the same time effect a resilient-type tension between the two members. Accordingly, any excessive force which might be created by compressing the bag by means of a human hand would not cause the bag 11 to separate from the inner connecting member 23. It should also be pointed out that while a secure snap fitment arrangement is provided between the two connecting members, only a degree of force as required by a human hand is necessary to assemble the two connecting members with the bag therebetween. Another advantage of closure 10 is that it can be advantageously used with an enema nozzle with the nozzle appropriately positioned and the bag 11 placed on the toilet seat. As one continuously places more weight against the bag, liquid will be forced therefrom yet the closure 10 will not leak or become disengaged.

While the inner connecting member 23 has been indicated as being composed of a rigid high density polyethylene material, it should be understood that other rigid materials such as polypropylene could be employed. Accordingly, outer connecting member 31 was previously described as being composed of a flexible low density polyethylene material. Other flexible materials such as polypropylene could be substituted.

Feminine spray nozle 14 and rectal spray nozzle 15 are preferably formed in two pieces for ease in packaging. They are preferably formed from a flexible plastic material such as Kraton.

It will thus be seen that through the present invention there is now provided a secure closure means for a syringe bag which can be quickly assembled without excessive force yet excessive force employed on the syringe bag will not cause it to become dislodged. The closure means can be easily molded without any special molding techniques yet contains internal threads for engagement and disengagement with a nozzle member. The connector means when disassembled from the nozzle can be easily packaged in a substantially horizontal flat manner so as to be folded into a kit for traveling purposes.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A closure means for a syringe bag having a resilient neck portion with a bead comprising:
    a hollow nozzle member defining a hollow spray stem having an externally threaded inlet and an outlet end;
    a first connecting member defining a hollow body section with internal threads complementary to said external threads of said nozzle member;
    a support ledge member extending from said body section;
    a wall portion defined by said body section and spaced from said support ledge member;
    a second hollow connecting member defining two spaced flange members extending in the direction of the inside of said connecting member;
    said second connecting member constructed and arranged in relation to said first connecting member so that said first connecting member can be snap fitted within the confines of said second connecting member and retained by said flange members;
    whereby when said bead of said bag is placed over said support ledge member of said first connecting member and said first connecting member is placed in said second connecting member, said one of said flange members of said second connecting member will engage said wall portion of said first connecting member and said other flange member will resiliently hold a portion of said bag against said support ledge.

2. The closure means as defined in claim 1 wherein said first and second connecting members are of an annular configuration.

3. The closure means as defined in claim 2 wherein said bag includes an annular bead and said first connecting member includes a reduced diameter portion adjacent said support ledge and defining with said second hollow connecting member a compartment for said bead.

4. The closure means as defined in claim 1 wherein said first connecting member is composed of a rigid material and said second conecting member is composed of a semirigid material.

5. The closure means as defined in claim 1 wherein said support ledge member is positioned adjacent the base wall of said first connecting member.

6. A closure means for a feminine or rectal syringe bag having a resilient neck portion and nozzle with external connecting means comprising:
- a first connecting member defining a hollow body section with internal connecting means complementary to said external connecting means of said nozzle;
- a support ledge member extending from said body section;
- a wall portion defined by said body section and spaced from said support ledge member;
- a second hollow connecting member defining two spaced flange members extending in the direction of the inside of said connecting member;
- said second connecting member constructed and arranged in relation to said first connecting member so that said first connecting member can be snap fitted within the confines of said second connecting member and retained by said flange members;

whereby when said bead of said bag is placed over said support ledge member of said first connecting member and said first connecting member is placed in said second connecting member, said one of said flange members of said second connecting member will engage said wall portion of said first connecting member and said other flange member will resiliently hold a portion of said bag against said support ledge.

7. The closure means as defined in claim 6 further including a container for all of said components and said nozzle connecting means disengaged from said connecting means of said first connecting member whereby all of said components can be packaged in a substantially flat plane.

8. The closure means as defined in claim 7 wherein said connecting means are threads.

* * * * *